United States Patent [19]

Seiler et al.

[11] Patent Number: 5,087,714

[45] Date of Patent: Feb. 11, 1992

[54] METHOD OF PREVENTING DISCOLORATION OF VINYLACETOXYSILANES

[75] Inventors: Claus-Dietrich Seiler; Hartwig Rauleder; Albert Frings; Hans-Joachim Kötzsch, all of Rheinfelden, Fed. Rep. of Germany

[73] Assignee: Huels Aktiengesellschaft, Marl, Fed. Rep. of Germany

[21] Appl. No.: 709,593

[22] Filed: Jun. 3, 1991

[30] Foreign Application Priority Data

Jul. 9, 1990 [DE] Fed. Rep. of Germany ....... 4021869

[51] Int. Cl.$^5$ ............................................. C07F 7/08
[52] U.S. Cl. ................................................... 556/401
[58] Field of Search ........................................ 556/401

[56] References Cited

U.S. PATENT DOCUMENTS

| | | | |
|---|---|---|---|
| 2,697,114 | 12/1954 | Cheuicek | 556/401 |
| 2,698,836 | 1/1955 | Morrell | 556/401 X |
| 4,780,555 | 10/1988 | Bauh | 556/401 X |
| 4,798,889 | 1/1989 | Plueddemann et al. | 556/401 |
| 4,927,948 | 5/1990 | Berkhardt et al. | 556/401 |

*Primary Examiner*—Paul F. Shaver
*Attorney, Agent, or Firm*—Felfe & Lynch

[57] ABSTRACT

Discoloration of vinylacetoxysilanes is prevented by adding thereto 25 to 500 ppm, based on the amount of vinylacetoxysilane, of 3,5-di-tert.-butylpyrocatechol, 2,6-di-tert.-butyl-4-methylphenol, 2-mercaptobenzimidazole or a mixture thereof.

3 Claims, No Drawings

METHOD OF PREVENTING DISCOLORATION OF VINYLACETOXYSILANES

FIELD OF THE INVENTION

The present invention relates to a novel method of preventing the discoloration of vinylacetoxysilanes.

BACKGROUND OF THE INVENTION

Vinylacetoxysilanes have a broad variety of applications in the chemical industry. For instance, they are useful as cross-linking silicon compounds for the preparation of compositions which have a long shelf life under exclusion of moisture and are curable at room temperature on contact with moisture to produce elastomers. Such compositions are obtained by mixing diorganopolysiloxanes containing condensable terminal groups with cross-linking silicon compounds. They also play an important role as intermediates or precursors for the preparation of compounds whose distillative purification is not without problems due to thermal instability, such as, for example, vinyltris(butanone oximato)silane.

Vinylacetoxysilane compounds can be prepared by various routes. For example, these compounds may be prepared by reacting vinylchlorosilanes with acetic acid anhydride, which produces acetyl chloride as a by-product. Vinylacetoxysilanes may also be prepared by reacting vinylchlorosilanes with acetic acid, predominantly in an inert medium. The reaction of vinylalkoxysilanes with acetic acid anhydride also results in the formation of vinylacetoxysilanes, although this method does not achieve the economic efficiency of the other above mentioned synthetic routes.

The vinylacetoxysilane products obtained by means of the above described methods have the serious disadvantage that the distillates take on a yellow to dark brown color at varying rates, that is after a few days or a few weeks subsequent to packaging. Even vinylacetoxysilanes of especially high purity, obtained by repeated fractional distillation of the products, discolor as quickly as products of only technical grade purity. Since the use of discolored vinylacetoxysilanes is not acceptable because of adverse effects upon the secondary products, long-term storage of products of this type has heretofore not been possible.

OBJECTS OF THE INVENTION

It is an object of the present invention to provide a method for the preparation of vinylacetoxysilanes which do not discolor as these compounds frequently do shortly after their preparation, and remain resistant to discoloration for long periods of time, that is, for periods of more than one year.

Other objects and advantages of the present invention will become apparent as the description thereof proceeds.

DESCRIPTION OF THE INVENTION

We have discovered that the above object is achieved and vinylacetoxysilanes which are resistant to discoloration are obtained by admixing previously prepared vinylacetoxysilanes with 3,5-di-tert.-butyl-pyrocatechol, 2,6-di-tert.-butyl-4-methylphenol, 2-mercaptobenzimidazole or mixtures of any two or three of these, in amounts of 25 to 500 ppm at temperatures below 70° C.

The color of vinylacetoxysilanes prepared in this manner does not change even over a relatively long period of time because of the presence of the above additives. The present invention, therefore, also relates to vinylacetoxysilanes which are stabilized against discoloration with 3,5-di-tert.-butylpyrocatechol, 2,6-di-tert.-butyl-4-methylphenol, 2-mercaptobenzimidazole or mixtures of any two or three of these, in amounts of 50 to 250 ppm.

The prevention of discoloration of vinylacetoxysilanes is also hereinafter referred to as color stabilization. The causes or reactions which result in discoloration of vinylacetoxysilanes are not known. Even repeated distillation of the vinyl compounds does not yield distillates or distillate fractions which remain free of discoloration upon standing. Neither can products which remain free of discoloration be prepared by carrying out the distillation of the vinylacetoxysilanes in the presence of the additives according to the present invention. Vinylacetoxysilane products prepared in that manner discolor just as quickly as the distillates obtained without addition of the additives according to the present invention. The desired color stabilization of vinylacetoxysilanes is surprisingly caused exclusively by adding the additives according to the present invention to the distillates immediately after production thereof. It is not necessary to carry out any additional measures; on the contrary, additional treatments or measures may negate the desired effect.

The color stabilization achieved with the aid of the additives according to the present invention is surprising inasmuch as it is known that acetoxysilanes are very reactive toward sulfhydryl and hydroxyl groups in that they react therewith to form acetic acid and the corresponding silicon compounds. This reaction is of secondary importance in the present case, so that the additives according to the present invention which cause the color stabilization are not consumed therein, but instead remain available to suppress the reaction which results in the discoloration.

Suitable color stabilizers within the context of the present invention are 3,5-di-tert.-butylpyrocatechol, 2,6-di-tert.-butyl-4-methylphenol, and 2-mercaptobenzimidazole. Vinylacetoxysilanes are liquids at room temperature. Therefore, the color stabilization additives according to the present invention, which are solids at room temperature, are advantageously added to the vinylacetoxysilanes to be stabilized in the form of a solution. The solvent used for this purpose is preferably the vinylacetoxysilane itself which is to be stabilized. The preferred additive for color stabilization of vinylacetoxysilanes is 3,5-di-tert.-butylpyrocatechol.

The amounts of the individual additives to be used in each case vary and should be determined from case to case. In general, amounts of 100 to 250 ppm, based on the amount of vinylacetoxysilane to be stabilized, are sufficient. Even the addition of 25 ppm produces color stabilization. An amount of 50 to 250 ppm is preferred. The addition of amounts above 500 ppm is possible, but the addition of such large amounts produces no further improvement in the color stability of vinylacetoxysilanes. Mixtures of the additives according to the present invention can also be added to the vinylacetoxysilanes to stabilize them, provided that no reactions which impair the serviceability toward the discoloration mechanism occur with one another when they are admixed.

The addition of the color stabilizing additives of the present invention to the vinylacetoxysilanes is carried out at room temperature. If possible, heating to temperature above 70° C. should be avoided, since the aforesaid competing reaction with the acetoxy groups of the silane can occur beginning at this temperature, which may result in a reduction in the effectiveness of the color stabilizing compounds which are employed.

The following examples illustrate the present invention and will enable others skilled in the art to understand it more completely. It should be understood, however, that the invention is not limited solely to the particular examples given below.

COMPARATIVE EXAMPLE A 1292 g (8 mols) of vinyltrichlorosilane together with 700 ml of hexane were introduced into a 4-liter double-jacketed flask equipped with a reflux condenser, stirrer, dropping funnel and thermometer, and the contents were heated with the aid of a temperature-controlled circulating heating device. The mixture in the flask was heated to the boiling point, and then 1500 g of acetic acid were added over a period of 3 hours. The hydrogen chloride released by the reaction was continuously removed by suction, and the reaction mixture was maintained at the boiling point until the evolution of hydrogen chloride ceased.

The product which remained in the flask after the hydrogen chloride was removed was transferred into a distillation apparatus, and the hexane was removed by vacuum distillation. In order to remove the residual chlorine, an amount of sodium acetate, dissolved in glacial acetic acid, equivalent to the residual chlorine content of the product in the distillation still was added thereto. The precipitated sodium chloride was filtered off, and the filtrate was subsequently worked up by vacuum distillation. A main fraction of 1710 g of vinyltriacetoxysilane with a purity of 99.3% was obtained. The product was as clear and colorless as water.

100 cm$^3$ of the distillate were stored in a glass bottle wrapped in dark foil, and it was checked daily for evidence of discoloration. After 13 days of standing the product had taken on a dark yellow color.

COMPARATIVE EXAMPLE B

Portions of the main fraction obtained in Comparative Example A were subjected to a further vacuum distillation and were then stored in dark foil-wrapped glass bottles as in Example A. After standing for 15 days the product had taken on a dark yellow color.

EXAMPLE 1

The main fraction obtained in accordance with Comparative Example A was divided into several portions, and amounts of 3,5-di-tert.-butylpyrocatechol, 2,6-di-tert.-butyl-4-methylphenol, 2-mercaptobenzimidazole or mixtures thereof were added to each portion so that mixtures of vinyltriacetoxysilane containing 25, 50, 100, 250, 500 and 1000 ppm of the color stabilizing compounds according to the present invention were formed. After storage for 18 months, the mixtures exhibited no color changes.

COMPARATIVE EXAMPLE C

Comparative Example A was repeated, but vinylmethyldichlorosilane was used in place of vinyltrichlorosilane. A main fraction of 1327 g of vinylmethyldiacetoxysilane with a purity of 99.1% was obtained. The distillate was as clear and colorless as water. 100 cm$^3$ of the product were stored in a glass bottle wrapped in dark foil, and the contents were checked daily for evidence of discoloration. After 22 days the contents of the bottle had taken on a brownish color.

EXAMPLE 2

The main fraction obtained in Comparative Example C was divided into several portions, and amounts of 3,5-di-tert.-butylpyrocatechol, 2,6-di-tert.-butyl-4-methylphenol, 2-mercaptobenzimidazole or mixtures thereof were added to each portion so that mixtures of vinylmethyldiacetoxysilane containing 25, 50, 100, 250, 500 and 1000 ppm of the color stabilizing compounds according to the present invention were formed. After storage for 12 months, the mixtures exhibited no color changes.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of preventing the discoloration of a vinylacetoxysilane during storage, which comprises admixing a freshly prepared vinylacetoxysilane at a temperature between room temperature and 70° C. with 25 to 500 ppm, based on the amount of vinylacetoxysilane, of a compound selected from the group consisting of 3,5-di-tert.-butylpyrocatechol, 2,6-di-tert.-butyl-4-methylphenol, 2-mercaptobenzimidazole and mixtures thereof.

2. The method of claim 1, wherein the vinylacetoxysilane is admixed with 50 to 250 pp of the said compounds.

3. A color-stabilized vinyltriacetoxysilane containing 50 to 250 ppm, based on the vinyltriacetoxysilane, of a compound selected from the group consisting of 3,5-di-tert.-butylpyrocatechol, 2,6-di-tert.-butyl-4-methylphenol, 2-mercaptobenzimidazole and mixtures thereof.

* * * * *